United States Patent [19]

Casey et al.

[11] Patent Number: 4,716,203

[45] Date of Patent: Dec. 29, 1987

[54] DIBLOCK AND TRIBLOCK COPOLYMERS

[75] Inventors: Donald J. Casey, Ridgefield; Peter K. Jarrett, Trumbull; Louis Rosati, Norwalk, all of Conn.

[73] Assignee: American Cyanamid Company, Stamford, Conn.

[21] Appl. No.: 903,797

[22] Filed: Sep. 5, 1986

[51] Int. Cl.$^4$ .................. C08L 71/02; C08G 63/06
[52] U.S. Cl. .................. 525/408; 128/1 R; 128/335.5; 524/916; 528/361; 528/370; 525/450
[58] Field of Search ............... 525/408, 450; 528/361, 528/370; 524/916; 128/1 R, 335.5

[56] References Cited

U.S. PATENT DOCUMENTS

| | | | |
|---|---|---|---|
| 4,047,533 | 9/1977 | Perciaccante et al. | 128/335.5 |
| 4,438,253 | 3/1984 | Casey et al. | 528/86 |
| 4,452,973 | 6/1984 | Casey et al. | 528/354 |

*Primary Examiner*—Theodore E. Pertilla
*Attorney, Agent, or Firm*—Charles F. Costello, Jr.

[57] ABSTRACT

A diblock copolymer is disclosed having a first block of a polyalkylene oxide and a second block of glycolic acid ester and trimethylene carbonate linkages. A triblock copolymer is disclosed having a middle block obtained from an ethylene oxide homopolymer or a copolymer of ethylene oxide and a cyclic ether. Alternatively, the triblock copolymer middle block is obtained from a copolymer of formula (I):

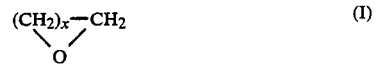

and formula (II):

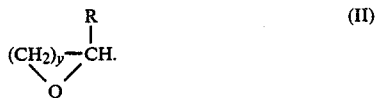

The copolymers are useful in medical and surgical applications.

16 Claims, No Drawings

DIBLOCK AND TRIBLOCK COPOLYMERS

BACKGROUND AND SUMMARY OF THE INVENTION

This invention relates to diblock and triblock copolymers. The diblock copolymer has a first block comprising a polyalkylene oxide and a second block consisting essentially of glycolic acid ester and trimethylene carbonate linkages.

The triblock copolymer has a middle block obtained by removing both terminal hydroxyl hydrogens from either a homopolymer of ethylene oxide, or from a copolymer of ethylene oxide and a cyclic ether. Alternatively, the triblock copolymer has a middle block obtained by removing both terminal hydroxyl hydrogens from a copolymer of a first cyclic ether selected from the group consisting of

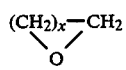

wherein x is 2 to about 9, and a second cyclic ether selected from the group consisting of

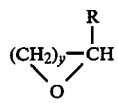

wherein y is 1 to about 9 and R is a $C_1$ to $C_6$ alkyl group.

The diblock and triblock copolymers of this invention are preferably bioabsorbable. They are useful as a coating, and/or as a lubricant, for example as a lubricating finish from a braided multifilamentary material. The diblock and triblock copolymers of this invention are also useful as a hydrogel, for example as an ingredient in a medical or surgical device or in a pharmaceutical composition.

A diblock copolymer has been invented. The copolymer has a first block comprising a polyalkylene oxide and a second block consisting essentially of glycolic acid ester and trimethylene carbonate linkages. In one embodiment, the polyalkylene oxide block is from 5 to 25 percent by weight of the copolymer. In another embodiment, the number average molecular weight of the polyalkylene oxide block is from about 4,000 to 30,000. In yet another embodiment, the polyalkylene oxide block is derived from a polyalkylene oxide terminated on one end by a $C_1$ to $C_6$ alkyl group and on the other end by a hydroxyl group.

In a specific embodiment of any of the above embodiments, the polyalkylene oxide block is derived from a homopolymer of ethylene oxide. In another specific embodiment of any of the above, the polyalkylene oxide block is derived from a block or random copolymer of ethylene oxide and a cyclic ether. In a more specific embodiment, the cyclic ether is selected from the group consisting of

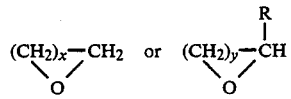

wherein x is 2 to about 9, y is 1 to about 9 and R is a $C_1$ to $C_6$ alkyl group.

In yet another specific embodiment, the polyalkylene oxide block is derived from a block or random copolymer of a first cyclic ether selected from the group consisting of

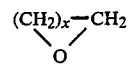

wherein x is 2 to about 9, and a second cyclic ether selected from the group consisting of

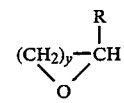

wherein y is 1 to about 9 and R is a $C_1$ to $C_6$ alkyl group.

In a more specific embodiment (to the above specific embodiments), a bioabsorbable diblock copolymer has been invented. The inherent viscosity of the copolymer, as measured at 30° C. for a 0.5% (w/v) solution in chloroform or methylene chloride, is 0.25 to about 1.50 dl/g.

A triblock copolymer has also been invented. The triblock copolymer is useful in nonfiber form. The middle block is obtained by removing both terminal hydroxyl hydrogens either form a homopolymer of ethylene oxide, or from a block or random copolymer of ethylene oxide and a cyclic ether. In one embodiment, the cyclic ether is selected from the group consisting of

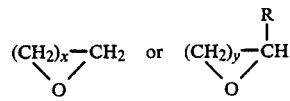

wherein x is 2 to about 9, y is 1 to about 9 and R is a $C_1$ to $C_6$ alkyl group.

Further, an alternative triblock copolymer has been invented. The alternative triblock copolymer is useful in nonfiber form. The middle block is obtained by removing both terminal hydroxyl hydrogens from a block or random copolymer of a first cyclic ether selected from the group consisting of

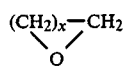

wherein x is 2 to about 9, and a second cyclic ether selected from the group consisting of

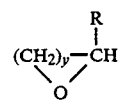

wherein y is 1 to about 9 and R is a $C_1$ to $C_6$ alkyl group.

In a further embodiment of any of the above embodiments, each end block of the triblock copolymer consists essentially of glycolic acid esters and trimethylene carbonate linkages. In a specific embodiment, the middle block is from 5 to 25 percent by weight of the copolymer. In a more specific embodiment, the number average molecular weight of the middle block is from about 4,000 to 30,000.

In a most specific embodiment (to the above specific embodiments), a bioabsorbable triblock copolymer has been invented. The inherent viscosity of the copolymer, as measured at 30° C. for a 0.5% (w/v) solution in chloroform or methylene chloride, is 0.25 to about 1.50 dl/g.

DESCRIPTION OF THE INVENTION

This invention relates to diblock and triblock copolymers. The preparation of degradable thermoplastic hydrogels consisting of the block polymers, as well as to other utility, such as a coating and lubricating finish for surgical articles including sutures is described.

The block copolymers will impart lubricity to, and improve the tie-down properties of multifilament absorbable sutures in both wet and dry state. In addition, these materials are capable of being completely degraded and eliminated from the body over a period of time. A particular advantage of these materials is their thermoplastic nature, that is, they can be applied to sutures by conventional solution or thermal techniques.

Recently, there has been interest in using hydrogels in a wide variety of biomedical (including veterinary) applications such as contact lenses, burn dressings, blood and tissue compatible implants, lubricant coatings for surgical implants, and drug delivery devices. In some of these areas, crosslinked hydrogel materials have met with great success. However, these materials suffer drawbacks, such as a lack of processibility, which are a consequence of their crosslinked nature.

Our approach to this problem was to investigate the use of block copolymers as theremoplastic biodegradable hydrogels for suture coating applications. In an ABA triblock example of these block polymers, the middle (B) block is a water soluble polymer such as a poly(alkylene oxide) and the end blocks (A) are comprised of degradable random copolymers of glycolide (Gly) and trimethylene carbonate (TMC). The middle and end blocks of this block copolymer are chemically incompatible and the result is a phase separated system with poly(alkylene oxide) regions dispersed throughout the Gly/TMC matrix. When exposed to an aqueous environment, the block polymer picks up an amount of water which is a function of the composition and molecular weight of the various block structures. The thermoplastic nature of the block polymers allows for lubricant coatings to be applied by known solution or melt processes. The crystalline poly(alkylene oxide) segments serve, in the dry state, as temperature dependent crosslinks which hold the coating securely in place and minimize coating flow on storage of the surgical suture.

The method of choice for preparing the above block copolymers is the melt phase ring-opening copolymerization of glycolide and trimethylene carbonate using specially purified, commercially available difunctional or monofunctional poly(alkylene glycols) as initiators. These polymerizations are conducted in a stirred reactor at about 165° C. under nitrogen. When maximum melt viscosity has been reached, the polymer is discharged and allowed to cool to room temperature. Oligomeric material can be removed by reprecipitation from methylene chloride solutions into methanol or ethanol.

Samples of the above polymers are extruded at 60°-100° C. with an extruder to yield fibers of 1.5 mm average diameter. The fibers are then cut into 1" lengths and several are placed in deionized water at room temperature. At various time intervals, the fibers are withdrawn, wiped thoroughly to remove any surface liquid, and the water uptake is measured gravimetrically. Alternatively, the uptake can be measured from thin films (0.6 mm) prepared by compression molding the polymer at 90° C., or by casting thin films of the polymer from solution.

The Above embodiments are more fully described in the following examples.

EXAMPLE 1

Purification of Materials

DL-lactide: DL-lactide was purchased from Purac, Inc. One kilogram of DL-lactide is refluxed for 1½ hours with toluene (1500 g) which has been dried by distillation from benzophenone ketyl. The residual water is removed from the DL-lactide by collection of the toluene/water azeotrope in a Dean-Stark trap. The dry DL-lactide solution is allowed to cool to room temperature and placed in the refrigerator overnight. The crystallized DL-lactide is then quickly filtered and dried in a vacuum over at room temperature. Recrystallization yield is 84%.

Polyethylene Glycol-8,000: Polyethylene glycol-8,000 (PEG 8,000) (160 g) is dissolved in methanol (1600 ml). The PEG solution is then freed of catalyst impurities and deionized by slowly passing the solution through a methanol conditioned indicating mixed bed anionic and cationic ion-exchange resin (Amberlite MB-3, Rohm and Haas Company, PA, U.S.A.). After elution from the column, the PEG is crystallized by placing the solution in a freezer overnight. The crystalline PEG is then filtered and air dried for 2 hours. The PEG is further purified by recrystallization from acetone (1600 ml). The recrystallized PEG is filtered and dried in a vacuum oven at room temperature overnight. Prior to polymerization, the desired amount of purified PEG is dried further by heating in a vacuum oven at 70° C. with $P_2O_5$ as a desiccant. PEG-14,000 and PEG-20,000 are purified in the same way.

Pluronic F68:

Pluronic F68 was purified by the same technique as described for PEG above but without the acetone recrystallization step. The methanol recrystallized Pluronic F68 was filtered and dried in a vacuum oven at room temperature. Prior to polymerization, the Pluronic F68 was further dried by heating in a vacuum oven at 70° C. with $P_2O_5$ as a desiccant.

Pluronic P105:

Pluronic P105 was purified by the same method described for PEG above. The polymer was recovered from the methanol solution using a rotary evaporator. Residual methanol was removed by drying in vacuum to constant weight. The material was not recrystallized from acetone. Prior to polymerization the Pluronic P105 was dried further by heating in a vacuum oven at 50° C. with $P_2O_5$ as a desiccant.

Polyethylene Glycol Methyl Ether: Polyethylene glycol methyl ether, nominal molecular weight 5000, was purified in the same way as described for PEG above.

EXAMPLE 2

Synthesis of (Gly/TMC)-(PEO 14,000)-(Gly/TMC) ABA Triblock Copolymer (gly/PEO/TMC: 34/41/25)

A 250 ml flask is charged with PEG-14000 (50 g, 0.0036 mole). The flask is placed in a vacuum oven and the PEG is dried overnight under vacuum at 70° C. with P$_2$O$_5$ as a drying agent. The flask is then placed in a glove bag under N$_2$. Glycolide (25.0 g, 0.21 mole) and trimethylene carbonate (25.0 g, 0.24 mole) are charged to the flask and the contents are melted and mixed under N$_2$. The monomer mixture is then quickly transferred into a stirred reactor which has been heated under a nitrogen flow to 165° C. Stannous octoate (0.16 ml, 4.9×10$^{-4}$ mole) is then quickly charged to the reactor with the use of a syringe. The polymer melt is stirred at 40 rpm for approximately 3 hours at 165° C. This time period corresponds to a maximum in the melt viscosity. The polymer is discharged from the reactor and allowed to cool to room temperature. A portion of the crude polymer (42.8 g) is dissolved in CH$_2$Cl$_2$ (250 ml) and reprecipitated dropwise into rapidly stirred absolute ethanol (3000 ml). After filtration and drying to constant weight, the reprecipitation yield was determined to be 96%. The inherent viscosity of the polymer (0.5 g/dL, in CHCl$_3$ at 30° C.) was 0.38 dL/g. The composition was analyzed by $^1$H-NMR and was found to be 34/41/25 weight percent Gly/PEO/TMC. The Tg of the polymer was 11° C., the melting point (Tm) was 59° C.

EXAMPLES 3–14

Several polymers were prepared as in Example 2 with varying PEG contents and PEG molecular weights (Table I). In many of the Gly/PEO/TMC triblock copolymers, the charged ratio of Gly/TMC is 60/40 weight percent. This allows for maximum Tg of the rubbery end blocks (9° C.) while still maintaining solubility in common organic solvents. Differential scanning calorimetry (DSC) clearly shows phase separation in these materials. The Tg of the rubbery end blocks (7°–16° C.) is very close to the Tg of a 60/40 random Gly/TMC polymer. In addition, the Tm of the crystalline PEO segments are only lowered 5°–10° C.

EXAMPLE 15

Synthesis of (Gly/TMC)-(PEO-8000)-(Gly/TMC) ABA, (Gly/PEO/TMC: 59/6/35)

Glycolide (117.0 g, 1.01 mole), trimethylene carbonate (71.0 g, 0.70 mole), PEG-8000 (12.0 g) and stannous octoate (0.33 ml, 1.0×10$^{-3}$ mole) were combined in a stirred reactor as in Example 2. The reaction mixture was then stirred at 169° C. and 36–40 rpm for 1.5 hours. The polymer was recovered as in Example 2. The properties of this polymer are summarized in Table I.

EXAMPLE 16

Synthesis of (Gly/TMC)-(PEO-8000)-(Gly/TMC) ABA, (Gly/PEO/TMC: 54/8/38)

Glycolide (110.4 g, 0.95 moles), trimethylene carbonate (73.6 g, 0.72 moles), PEG-8000 (16.0 g) and stannous octoate (0.32 ml, 9.96×10$^{-4}$ moles) were combined and allowed to polymerize as in Example 15. The properties of this polymer as summarized in Table I.

EXAMPLE 17

Synthesis of (Gly/TMC)-(PEO-8000)-(Gly/TMC) ABA, (Gly/PEO/TMC: 54/10/36)

Glycolide (108.0 g, 0.93 moles), trimethylene carbonate (72.0 g, 0.71 moles), PEG-8000 (20.0 g) and stannous octoate (0.32 ml, 9.96×10$^{-4}$ moles) were combined and allowed to polymerize as in Example 15. The properties of this material are summarized in Table I.

TABLE I

Glycolide/PEO/TMC Polymers

| Example | Charged Composition (Gly/PEO/TMC Wgt. %) | PEG MW | $\eta_{inh}$ (Solvent) As Polymerized | $\eta_{inh}$ (Solvent) Reprecipitated | Gly/PEO/TMC Composition by $^1$H—NMR (wt %) As Polymerized | Gly/PEO/TMC Composition by $^1$H—NMR (wt %) Reprecipitated | Tg (°C.) | Tm (°C.) |
|---|---|---|---|---|---|---|---|---|
| 3 | 25/50/25 | 14,000 | — | 0.40 (CHCl$_3$) | — | 30/43/27 | — | — |
| 4 | 32/50/18 | 14,000 | — | 0.45 (CH$_2$Cl$_2$) | — | 31/54/14 | — | — |
| 5 | 48/20/32 | 14,000 | — | 0.45 (CHCl$_3$) | — | 49/19/32 | 16 | 57 |
| 6 | 54/10/36 | 14,000 | — | 0.34 (CH$_2$Cl$_2$) | — | 55/11/34 | 12 | 54 |
| 7 | 42/30/28 | 14,000 | 0.45 (CH$_2$Cl$_2$) | 0.45 (CH$_2$Cl$_2$) | — | 44/29/27 | 15 | 58 |
| 8 | 42/30/28 | 8,000 | 0.40 (CH$_2$Cl$_2$) | 0.38 (CH$_2$Cl$_2$) | — | 43/31/26 | 16 | 55 |
| 9 | 48/20/32 | 8,000 | 0.42 (CH$_2$Cl$_2$) | — | 48/21/31 | — | 14 | 55 |
| 10 | 54/10/36 | 8,000 | 0.46 (CH$_2$Cl$_2$) | 0.33 (CHCl$_3$) | 50/10/40 | 50/8/42 | 10 | 53 |
| 11 | 54/10/36 | 20,000 | — | — | — | — | 7 | 47 |
| 12 | 48/20/32 | 20,000 | — | — | — | — | 6 | 52 |
| 13 | 42/30/28 | 20,000 | — | — | — | — | 11 | 54 |
| 14 | 57/5/38 | 8,000 | 0.41 (CHCl$_3$) | 0.38 (CHCl$_3$) | 57/5/38 | 58/5/37 | — | — |
| 15 | 58/6/36 | 8,000 | 0.42 (CHCl$_3$) | 0.40 (CHCl$_3$) | 59/6/35 | 59/6/35 | — | — |
| 16 | 55/8/37 | 8,000 | 0.44 (CHCl$_3$) | 0.42 (CHCl$_3$) | 53/8/39 | 54/8/38 | — | — |
| 17 | 54/10/36 | 8,000 | 0.45 (CHCl$_3$) | 0.40 (CHCl$_3$) | 54/10/36 | 54/10/36 | — | — |

EXAMPLE 18

Synthesis of (Gly/dl-Lact)-(PEO-8000)-(Gly/dl-Lact) ABA, (Gly/dl-Lact/PEO: 36/54/10)

Glycolide (54.0 g, 0.46 moles), dl-lactide (81.0 g, 0.56 moles), PEG-8000 (15.0 g) and stannous octoate (0.32 ml, 9.96×10$^{-4}$ moles) were combined and allowed to polymerize as in Example 2. The properties of this polymer are summarized in Table II.

EXAMPLE 19

Synthesis of (Gly/l-Lact)-(PEO-8000)-(Gly/l-Lact) ABA: (Gly/l-Lact/PEO: 27/65/8)

Glycolide (53.2 g, 0.46 moles), l-lactide (130.8 g, 0.91 moles), PEG-8000 (16.0 g) and stannous octoate (0.05 ml, 1.56×10$^{-4}$ moles) are combined and allowed to polymerize by the procedure described in Example 15. The properties of this polymer are summarized in Table II.

EXAMPLE 20

Synthesis of (l-Lact/TMC)-(PEO-8000)-(l-Lact/TMC) ABA, (l-Lact/TMC/PEO: 43/49/8)

l-Lactide (88.0 g, 0.61 moles), trimethylene carbonate (96.0 g, 0.94 moles), PEG-8000 (16.0 g) and stannous octoate (0.31 ml, 9.74×10$^{-4}$ moles) are combined and allowed to polymerize by the procedure described in Example 15. The properties of this polymer are summarized in Table II.

EXAMPLE 21

Synthesis of
(Gly/dl-Lact)-(PEO-20,000)-(Gly/dl-Lact) ABA,
(Gly/dl-Lact/PEO: 21/25/54)

dl-lactide (25.0 g, 0.17 moles), glycolide (25.0 g, 0.21 moles), PEG 20,000 (50.0 g) and stannous octoate (0.16 ml, $4.94 \times 10^{-4}$ moles) are combined and allowed to polymerize by the procedure described in Example 2. The properties of this polymer are described in Table II.

sured gravimetrically. The water uptake is shown in Table III. From the values at 1280 min., the equilibrium water uptake for fibers was calculated to be 232±3%.

Water uptake analysis was performed on 4 samples of films of the polymer of Example 7 (12×4×0.6 mm). The results are shown in Table III. The shorter time to reach an equilibrium value of water uptake in the films is attributable to the greater surface-to-volume ratio in the films.

TABLE II

Terpolymers With PEO Midblocks and Various Endblocks

| Example | Charged Composition | PEG MW | $\eta_{inh}$ (Solvent) As Polymerized | Reprecipitated | Composition by $^1$H—NMR (Wt %) As Polymerized | Reprecipitated | Tg | Tm |
|---|---|---|---|---|---|---|---|---|
| 18 | Gly/dl-lactide/PEO: 36/54/10 | 8,000 | 0.49 (CHCl$_3$) | 0.35 (CHCl$_3$) | 36/54/10 | 36/54/10 | — | — |
| 19 | Gly/l-lactide/PEO: 27/65/8 | 8,000 | 0.73 (CHCl$_3$) | — | 27/65/8 | — | 36 | — |
| 20 | l-Lactide/TMC/PEO: 44/48/8 | 8,000 | 0.56 (CHCl$_3$) | — | 43/49/8 | — | 0 | — |
| 21 | Gly/dl-lactide/PEO: 25/25/50 | 20,000 | — | 0.43 (CHCl$_3$) | — | 21/25/54 | 42 | 57 |

EXAMPLE 22

Swelling Behavior of Examples 3, 4 and 21

A film was prepared by solution casting a 20% w/v solution of the polymer of Example 3 in CH$_2$Cl$_2$. After the solvent had evaporated overnight, the film was dried further under vacuum at room temperature overnight. Films made from the polymers of Example 3, 4 and 21 were placed in water at 37° C. with stirring. After 24 hours, films from Example 3 and Example 4 had formed emulsions. By day 3, the film from Example 21 had also formed an emulsion.

EXAMPLE 23

Swelling Behavior of Example 7 (Gly/PEO/TMC: 44/29/27)

A sample of the polymer from Example 7 (1.5 g) was extruded at 110° C. to yield a 1.5 mm diameter fiber. From the fiber 5 samples, lengths each approximately 1" were cut. The samples were placed in deionized water at room temperature. Periodically, the samples were withdrawn, wiped dry, and the water uptake measured.

TABLE III

Water Uptake by Fibers and Films of 44/29/27 Gly/PEO/TMC (Ex. 7)

| Fibers | | Films | |
|---|---|---|---|
| Time (min) | % H$_2$O$^A$ Uptake | Time (min) | % H$_2$O$^A$ Uptake |
| 5 | 31.1 | 5 | 136.7 |
| 18 | 60.9 | 22 | 238.7 |
| 32 | 89.3 | 35 | 271.0 |
| 45 | 107.9 | 63 | 279.5 |
| 65 | 133.6 | 81 | 282.2 |
| 90 | 158.2 | 216 | 279.1 |
| 118 | 183.7 | 363 | 253.5 |
| 148 | 204.3 | 1560 | 266.3 |
| 179 | 223.3 | | |
| 1155 | 237.6 | | |
| 1280 | 235.5 | | |

$A = \frac{(Wt\ Swollen - Wt\ Dry)}{Wt\ Dry} \times 100$

EXAMPLE 24

Swelling of Various Hydrogels

Water uptake experiments were carried out on fibers of several Gly/PEO/TMC hydrogels and one Gly/dl-Lactide/PEO hydrogel (Table IV). Measurements were carried out at room temperature in deionized water. All reported equilibrium uptake values are averages of 4 or 5 samples.

TABLE IV

Combined Swelling Data on Polymers

| Example | Polymer | PEG MW | PEO Content (Wgt. %) | % H$_2$O Uptake | Teq |
|---|---|---|---|---|---|
| 14 | Gly/PEO/TMC | 8,000 | 5 | 27.9 ± 5.4[1,3] | ~13 days |
| 10 | Gly/PEO/TMC | 8,000 | 8 | 124.1 ± 7.4[1,3] | ~1 day |
| 10 | Gly/PEO/TMC | 8,000 | 10 | 11.3 ± 0.9[1,2] | 4 |
| 18 | Gly/dl-lactide/PEO | 8,000 | 10 | 9.9 ± 1.3[1,3,5] | 5 |
| 9 | Gly/PEO/TMC | 8,000 | 21 | 163.0 ± 1.8[1,2] | 4 |
| 8 | Gly/PEO/TMC | 8,000 | 31 | 224.5 ± 15.1[1,3] | 4 |
| 6 | Gly/PEO/TMC | 14,000 | 11 | 125.8 ± 4.5[1,3] | 4 |
| 5 | Gly/PEO/TMC | 14,000 | 19 | 164.9 ± 11.2[1,3] | 4 |
| 7 | Gly/PEO/TMC | 14,000 | 29 | 235.9 ± 3.1[1,3] | ~17 hrs |
| 7 | Gly/PEO/TMC | 14,000 | 29 | 260.8 ± 10.3[3,6] | 20 min |
| 11 | Gly/PEO/TMC | 20,000 | 10 | 61.0 ± 0.5[1,2] | 4 |
| 12 | Gly/PEO/TMC | 20,000 | 20 | 169.0 ± 0.8[1,2] | 4 |

TABLE IV-continued

Combined Swelling Data on Polymers

| Example | Polymer | PEG MW | PEO Content (Wgt. %) | % H$_2$O Uptake | Teq |
|---|---|---|---|---|---|
| 13 | Gly/PEO/TMC | 20,000 | 30 | 289.2 ± 5.6[1,2] | 4 |

[1]fiber (dimensions = 10 mm × 1.5 mm diameter)
[2]as polymerized
[3]reprecipitated
[4]not determined
[5]not at equilibrium by day 13
[6]film (dimensions = 12 × 4 × 0.6 mm)

Several generalizations about the data in Table IV can be made. The time to reach an equilibrium value of water uptake depends on the shape of the sample (Example 7 fiber vs. film). It would also appear that the time to reach an equilibrium value of water uptake decreases as the PEO content increases.

Within the scatter in the data, equilibrium water uptake is linearly related to the PEO content in the range 5–30%. There is no noticeable effect of the MW of the PEO block on the swelling of these triblock polymers (within the range of PEO MW 8,000-20,000).

One important difference noted in Table IV is the contrast of Example 10 (Gly/PEO/TMC) with Example 18 (Gly/PEO/dl-Lactide). Both have approximately the same percent of PEO 8,000; however, a reprecipitated sample of Example 10 had an equilibrium water content of 124% (Teq 1 day) vs. 9.9% by day 13 for a reprecipitated sample of Example 18. The difference can be rationalized by looking at the differences of the two matrices. In the case of the sample of Example 10 the Gly/TMC matrix is free to deform to accommodate the dimensional changes caused by the swelling. With the sample of Example 18, however, the Gly/dl-Lactide matrix has a dry Tg of approximately 30° C. At room temperature, it is in a glassy state and cannot deform as easily to accommodate the dimensional changes necessary to swell. This should result in a slower water uptake curve (note that at 13 days equilibrium has not been reached) until the Gly/dl-Lactide matrix is sufficiently plasticized by water.

EXAMPLE 25

Suture Coating Experiments

Two methods are used to apply the coating polymer to an uncoated 1/0 polyglycolic acid braided suture. In the hand dip method, which is largely used to screen potential coating candidates, the braided strand is run under an inverted "U" guide mounted on a holder immersed in a solution of the coating polymer. Any solvent can be used that will dissolve the coating polymer and not damage the PGA braid. Typically, methylene chloride, chloroform, 1,1,1-trichloroethane, or acetone can be used as solvents. After each pass through the solution, the coated sutures are air dried in a hood. Several passes can be made through the solution to increase the amount of material picked-up on the braid. After the final pass, the braid is dried at room temperature and reduced pressure for 2–4 hours.

The preferred method of coating uses a pump to supply coating solution to a ceramic guide through which the PGA braid is passed at a controlled rate. The coated braid is then passed through a hot air oven to remove the coating solvent. This braid is cut, needled, sterilized, vacuum dried and packaged.

A general description for the coating of a surgical suture is as follows. A commercially available coater (e.g. from the Bouligny Co., U.S.A.) is set to operate on a filament traveling at a speed of 50 feet per minute. The circulating air in the drying oven is adjusted to be 80° C.

There is only one pass of the filament through the capillary coating apparatus, and then through the drying oven. The coating pump is adjusted to give about 5 to 8 drops per minute at the capillary apparatus.

Using the above coating method, the percent pickup is about 3.5 to 3.6 percent based on the weight of the filament. It is to be understood that this amount of pickup can be increased or decreased by an person skilled in the art without undue experimentation by adjusting the above parameters. Preferably, the amount of pickup is increased by decreasing the amount of solvent in the coating formulation, and vice versa.

The dip-coated braid and the machine coated braid are easily tested for improvements provided by the coating to both knot repositioning and knot security. Size 1/0 PGA braid samples were coated with several Gly/PEO/TMC terpolymers (Table V) and with three lactide based terpolymers (Table VI).

TABLE V

| | | In Vitro Coating Performance: Gly/PEO/TMC Terpolymers | | | | |
|---|---|---|---|---|---|---|
| | | Pick-Up | Knot | Knot | Knot Run Down[4] | |
| | Coating Polymer | (Wt %)[1] | Repositioning (mm)[2] | Security (mm)[3] | Wet | Dry |
| Control | No Coating | 0 | 2.8 | 1.6 | — | — |
| Ex. 5 | Gly/PEO/TMC: 49/19/32 | 0.4 | 22.4 | 10.0 | RW | RW |
| Ex. 14 | Gly/PEO/TMC: 58/5/37 | 0.3 | 3.0 | 2.0 | L | — |
| Ex. 15 | Gly/PEO/TMC: 59/6/35 | 0.9 | 15.0 | 5.1 | L | RD |
| | | 1.8 | 19.6 | 7.8 | RC | RC |
| | | 2.6 | 18.8 | 4.9 | RC | RC |
| Ex. 16 | Gly/PEO/TMC: 54/8/38 | 1.1 | 27.7 | 9.7 | RC | RW |
| | | 1.9 | 28.0 | 12.8 | RW | RW |
| | | 2.7 | 28.2 | 14.4 | RW | RW |
| Ex. 17 | Gly/PEO/TMC: 54/10/36 | 0.9 | 27.9 | 8.2 | RC | RW |
| | | 1.8 | 27.7 | 7.5 | RC | RW |
| | | 2.3 | 27.7 | 6.7 | RW | RW |

TABLE V-continued

TABLE V FOOTNOTES (1) The coatings were applied to 1/0 polyglycolic acid braid from a 2% (wt/vol.) solution of the coating material dissolved in methylene chloride.

(2) This test measures the ability of a suture to be snugged in. A loop is passed around a steel rod and tied with a square knot. The knot is set to a prescribed tension with an Instron tester, and the tension is then removed. After resetting the gage length, the loop is tested to break. The breaking strength of the loop and elongation-to-break are recorded. The material elongation at the point of knot break is determined separately in a straight pull test, and subtracted from the knot breaking elongation to obtain the slippage in mm within the knot up to the breaking point. Samples were tested immediately after 30 seconds immersion in saline solution (0.9% NaCl in distilled water). The tensions used to set the knots, and all the other conditions of knot tying and testing, are practical laboratory conditions, but may not correspond to actual surgical practice. The knot snug in may not correlate with clinical experience.

(3) A strand is tied to itself to form a loop, the knot is set to a prescribed tension, the loop is cut, and the cut ends are clamped in the jaws of an Instron tester. The breaking strength and elongation-to break are measured. The maximum slippage is recorded for the knots that break. This is defined as the difference between the average elongation-to-break of the knotted suture and the average elongation of an unknotted strand, measured at a load equal to the knot breaking strength. Samples are tested immediately after 30 seconds immersion in saline solution.

(4) Square knots were formed in hand-dipped 1/0 polyglycolic acid braid using a conventional suture tying board. The knot was then run down to the board to assess the stick-slipping of the knot (chatter) as it runs down and to assess the force required to initiate and sustain the run-down. The abbreviations are: L, Lock; RC, Runs with Chatter; RD, Runs with Difficulty; RW, Runs Well. The comparisons are made on dry suture and on suture wet with saline.

TABLE VI

In Vitro Coating Performance: Terpolymers Made With Lactide

| Coating Polymer | | (Wt %) | Knot Run Down[1] | |
|---|---|---|---|---|
| | | | Wet | Dry |
| Ex. 19 | Gly/l-Lactide/PEO: 27/65/8 | 1-3 | L | L |
| Ex. 20 | l-Lactide/TMC/PEO: 43/49/8 | 1-3 | L | L |
| Ex. 21 | Gly/dl-Lactide/PEO: 21/25/54 | 1-3 | RW | RW |

[1]L: Locks; RW: Runs Well

From the in vitro data on knot repositioning with these coated braids, it is evident the Gly/PEO/TMC coatings with PEO contents as low as 6% permit easy movement of a square knot, whereas lactide base terpolymer coatings locked rather than reposition if the PEO content was low (~8%). However, if the PEO content was high in the lactide based terpolymer, the coating allowed for good repositioning, indicating that the minimum acceptable PEO content is dependent upon the end block composition.

EXAMPLE 26

A Gly/PEO/TMC 59/6/35 weight % polymer from Example 15 was dissolved in methylene chloride to give a 2% solids solution. A size 1/0 uncoated Dexon braid was immersed in this solution and dried. Multiple immersions were made so that different percent pick-up levels were obtained. A sample having 0.9% pick-up (based on the weight of the fiber) was later needled with a tapered needle, wound, packaged and sterilized using standard ethylene oxide sterilizing techniques. A surgeon used eight of these coated sutures to close a midlinie incision of a male dog, while evaluating the knot repositioning and the immediate knot security of these sutures.

EXAMPLE 27

Same as Example 26 except the polymer used was Gly/PEO/TMC 54/8/38 from Example 16.

EXAMPLE 28

Same as Example 26 except the polymer used was Gly/PEO/TMC 54/10/36 from Example 17.

EXAMPLE 29

Synthesis of (Gly/TMC) [Pluronic F68] (Gly/TMC) ABA (Gly/Pluronic F68/TMC: 56/8/36 PentaBlock Copolymer Pluronic F68 (BASF Wyandotte, U.S.A.) is a triblock copolymer of poly(ethylene oxide) (PEO) (80 mole %) and poly(propylene oxide) (PPO) (20 mole %) where PPO forms the middle block and the total molecular weight is about 8400. Like PEO, this copolymer is terminated with hydroxyl groups which can be used as an initiator for the ring opening polymerization of cyclic esters.

Glycolide (82.8 g), trimethylene carbonate (55.2 g), Pluronic F68 (12.0 g) and stannous octoate (0.242 ml), were combined in a stirred reactor as in Example 2. The reaction mixture was then stirred at 165° C. and 40 rpm for 1.5 hours. The polymer was recovered as in Example 2, and then characterized as follows: $\eta_{Inh}$ (CHCl$_3$): 0.40; Composition: 56/8/36 ($^1$H NMR); tg: 14° C.; Tm 42° C.

Table VII summarizes the in vivo ratings for 1/0 polyglycolic acid braid coated with the Gly/PEO/TMC block polymers, or with the block polymer containing a Pluronic F68 midblock of Examples 26 to 29.

TABLE VII

| | | In Vivo Coating Evaluations[1] | | | |
|---|---|---|---|---|---|
| | | Pick-Up | Knot Repositioning | Knot Security[4] | |
| Coating Polymer | | (Wt %)[2] | Ability[3] | Square | Square + 2 |
| Control | No Coating | 0 | 0/8 | 4/4 | 4/4 |
| Ex. 26 | Gly/PEO/TMC: 59/6/35 | 0.9 | 5/8 | 4/4 | 4/4 |
| Ex. 27 | Gly/PEO/TMC: 54/8/38 | 1.1 | 7/8 | 3/4 | 4/4 |
| Ex. 28 | Gly/PEO/TMC: 54/10/36 | 1.8 | 8/8 | 1/4 | 3/4 |
| Ex. 29 | Gly/F-68/TMC: 56/8/36 | 2.3 | 17/18 | — | 17/17 |

TABLE VII FOOTNOTES
(1) Coated, needled, and sterilized sutures were tested in dogs.
(2) The coatings were applied to 1/0 polyglycolic acid braid from a 2% (wt/vol) solution of the coating material dissolved in methylene chloride.
(3) A suture coated with the test material is passed through two sides of a wound in the animal. A square knot is formed in the suture approximately 12-15 mm from the final knot position required to close the wound. The two ends of the suture are then pulled to slide the knot into position. Knots that slide properly are rated 1 while knots that fail to move into position are rated 0. The rating for a coating is the sum of the "1" ratings divided by the total number of test specimens.
(4) Immediate knot security is determined by using a pair of curved tweezers to tug at the 8 to 10 mm length of the ears of a square knot or a square knot with two additional throws. Knots that are secure are rated 1 while knots that can be loosened are rated 0. The rating for a coating is the sum of the "1" ratings divided by the total number of test specimens.

EXAMPLE 30

Synthesis of (Gly/TMC) [Pluronic P105] (Gly/TMC) ABA (Gly/Pluronic P105/TMC: 56/9/35 PentaBlock Copolymer Pluronic P105 (BASF Wyandotte) is a triblock copolymer of poly(ethylene oxide) (PEO) (50 mole %) and poly(propylene oxide) (PPO) (50 mole %) where PPO forms the middle block and the total molecular weight is about 6500. Like PEO, this copolymer is terminated with hydroxyl groups which can be used as an initiator for the ring opening polymerization of a cyclic ester.

Glycolide (54 g), trimethylene carbonate (36 g) Pluronic P105 (10.0 g) and stannous octoate (0.19 ml), were combined in a stirred reactor as in Example 2. The reaction mixture was then stirred at 165° C. and 40 rpm for 1.5 hours. The polymer was recovered as in Example 2, and then characterized as follows: $\eta_{Inh}$ (CHCl$_3$): 0.35; Composition: 56/9/35 ($^1$H NMR).

A 1/0 polyglycolic acid braid was coated with 1 to 3% of this polymer. In in vitro knot-run-down tests with these coated sutures, square knots were found to run down well both wet and dry.

EXAMPLE 31

Synthesis of (PEO)-(Gly/TMC) AB (Gly/PEO/TMC: 57/6/37) Diblock Copolymer

Poly(ethylene glycol) methyl ether (PEO-5000) was purchased from Aldrich Chemical Company. The molecular weight was reported to be 5000. This polymer is terminated by one hydroxyl group and one methyl ether group. Only one end of this molecule, therefore, can be used to initiate the ring opening polymerization of cyclic esters, forming an AB diblock copolymer.

Glycolide (84.6 g), trimethylene carbonate (54.4 g) PEO 5000 (10.0 g) and stannous octoate (0.242 ml), were combined in a stirred reactor as in Example 2. The reaction mixture was then stirred at 165° C. and 40 rpm for 1.5 hours. The polymer was recovered as in Example 2, and then characterized as follows: $\eta_{Inh}$ (CHCl$_3$): 0.42; Composition: 57/6/37 ($^1$H NMR); tg: 12° C.; Tm: 59° C.

A 1/0 polyglycolic acid braid was coated with 1 to 3% of the polymer. In in vitro knot-run-down tests with these coated sutures, square knots were found to run down well both wet and dry.

We claim:
1. A diblock copolymer having a first block comprising a polyalkylene oxide and a second block consisting essentially of glycolic acid ester and trimethylene carbonate linkages.

2. A diblock copolymer of claim 1 wherein the polyalkylene oxide block is from 5 to 25 percent by weight of the copolymer.

3. A diblock copolymer of claim 1 or 2 wherein the number average molecular weight of the polyalkylene oxide block is from about 4,000 to 30,000.

4. A diblock copolymer of claim 1 or 3 wherein the polyalkylene oxide block is derived from a polyalkylene oxide terminated on one end by a $C_1$ to $C_6$ alkyl group and on the other end by a hydroxyl group.

5. A diblock copolymer of claim 4 wherein the polyalkylene oxide block is derived from a homopolymer of ethylene oxide.

6. A diblock copolymer of claim 4 wherein the polyalkylene oxide block is derived from a block or random copolymer of ethylene oxide, and a cyclic ether other than ethylene oxide.

7. A diblock copolymer of claim 6 wherein the cyclic ether is selected from the group consisting of

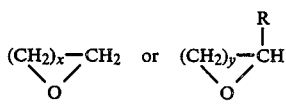

wherein x is 2 to about 9, y is 1 to about 9 and R is a $C_1$ to $C_6$ alkyl group.

8. A diblock copolymer of claim 4 wherein the polyalkylene oxide block is derived from a block or random copolymer of a first cyclic ether selected from the group consisting of

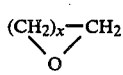

wherein x is 2 to about 9, and a second cyclic ether selected from the group consisting of

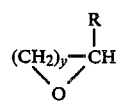

wherein y is 1 to about 9 and R is a $C_1$ to $C_6$ alkyl group.

9. A bioabsorbable diblock copolymer of claim 5 or 7 or 8 wherein the inherent viscosity of the copolymer, as measured at 30° C. for a 0.5% (w/v) solution in chloroform or methylene chloride, is 0.25 to about 1.50 dl/g.

10. A triblock copolymer useful in nonfiber form having a middle block obtained by removing both terminal hydroxyl hydrogens from either a homopolymer of ethylene oxide, or from a block or random copolymer of ethylene oxide and a cyclic ether.

11. A triblock copolymer of claim 10 wherein the cyclic ether is selected from the group consisting of

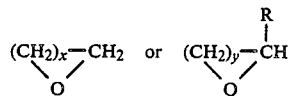

wherein x is 2 to about 9, y is 1 to about 9 and R is a $C_1$ to $C_6$ alkyl group.

12. A triblock copolymer useful in nonfiber form having a middle block obtained by removing both terminal hydroxyl hydrogens from a block or random copolymer of a first cyclic ether selected from the group consisting of

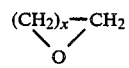

wherein x is 2 to about 9, and a second cyclic ether selected from the group consisting of

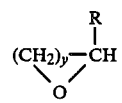

wherein y is 1 to about 9 and R is a $C_1$ to $C_6$ alkyl group.

13. A triblock copolymer of claim 11 or 12 wherein each end block of the triblock copolymer consists essentially of glycolic acid ester and trimethylene carbonate linkages.

14. A triblock copolymer of claim 11 or 12 or 13 wherein the middle block is from 5 to 25 percent by weight of the copolymer.

15. A triblock copolymer of claim 14 wherein the number average molecular weight of the middle block is from about 4,000 to 30,000.

16. A bioabsorbable triblock copolymer of claim 15 wherein the inherent viscosity of the copolymer, as measured at 30° C. for a 0.5% (w/v) solution in chloroform or methylene chloride, is 0.25 to about 1.50 dl/g.

* * * * *